United States Patent [19]

Gilson et al.

[11] 4,326,837

[45] Apr. 27, 1982

[54] PUMPING APPARATUS USING A STEPPING MOTOR

[75] Inventors: Robert E. Gilson; George W. Foster, both of Middleton, Wis.; Alain M. Bonneyrat, St-Martin-du-Tertre, France

[73] Assignee: Gilson Medical Electronics, Villiers-le-Bel, France

[21] Appl. No.: 99,867

[22] Filed: Dec. 3, 1979

[30] Foreign Application Priority Data

Dec. 15, 1978 [FR] France .............................. 78 35399

[51] Int. Cl.³ ............................................. F04B 49/00
[52] U.S. Cl. ....................................... 417/12; 417/22; 417/42; 417/45; 417/63; 417/415
[58] Field of Search ................... 417/1, 12, 20, 18, 22, 417/42, 44, 45, 63, 43, 271, 415

[56] References Cited

U.S. PATENT DOCUMENTS

| | | | |
|---|---|---|---|
| 3,471,079 | 10/1969 | Myers | 417/415 X |
| 3,966,358 | 6/1976 | Heimes et al. | 417/44 X |
| 4,137,011 | 1/1979 | Rock | 417/22 |
| 4,180,375 | 12/1979 | Magnussen | 417/45 X |
| 4,209,258 | 6/1980 | Oakes | 417/43 X |
| 4,221,543 | 9/1980 | Cosentino et al. | 417/22 |

Primary Examiner—Carlton R. Croyle
Assistant Examiner—Edward Look
Attorney, Agent, or Firm—Mason, Kolehmainen, Rathburn & Wyss

[57] ABSTRACT

A precision-delivery and precision-pressure piston pump is actuated by a cam controlled by a finestep stepping motor. The initial delivery pressure is precisely regulated by fixing the commencement of the delivery stroke at the cam with the aid of the stepping motor, as well as the time required for this delivery. Delivery is also regulated very precisely, for example in a ratio of 1 to 1000 by controlling the delivery stroke with the aid of the stepping motor. The pump is of use in particular in high-pressure liquid-phase chromatography.

12 Claims, 11 Drawing Figures

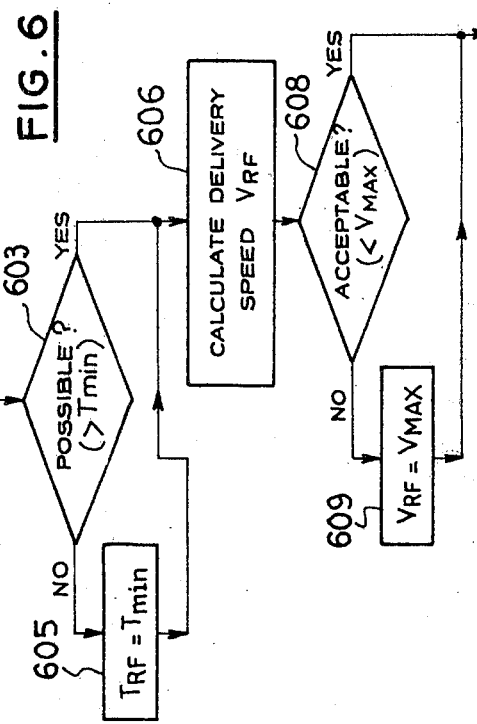
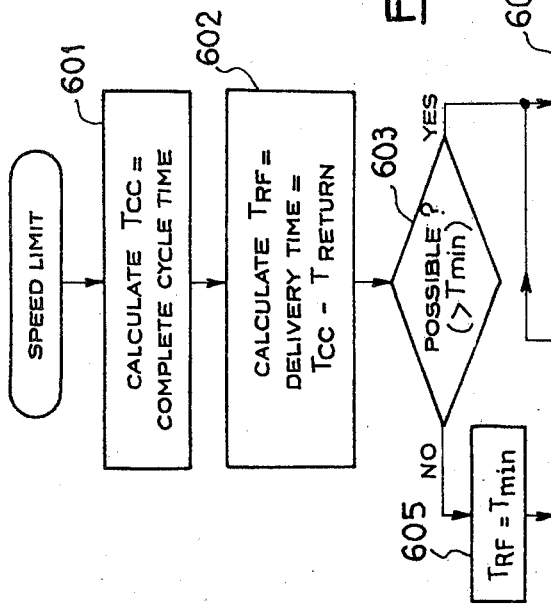
FIG. 6
FIG. 5

PUMPING APPARATUS USING A STEPPING MOTOR

BACKGROUND OF THE INVENTION

The present invention relates to precision pumps capable of providing a high downstream pressure.

Such pumps are used in particular in high-performance liquid-phase chromatography (HPLC), where they are used to inject one or more selected solvents into the lining, the substrate forming the stationary phase, of a chromatography installation. Since any fluctuation in pressure and/or in delivery is troublesome in this context, it is desirable to have a pump exhibiting virtually no such fluctuation. This problem is complicated by the fact that the pump must be capable of injecting a large variety of solvents and of adapting itself to linings of which the pressure drops also vary to a large extent.

Double-valve and single-piston pumps, actuated by a continuous-current motor, are known. In such cases it is a cam profile which defines a priori the top dead point and the bottom dead point of the piston as well as the relationship between the delivery time and the return time. As a general rule, such pumps produce considerable fluctuations in pressure, if not in delivery, in the chromatographic lining.

The use of pumps of the same kind but incorporating a number of pistons enables fluctuations in delivery and pressure to be reduced, but at the cost of considerable complexity and at much greater expense.

SUMMARY OF THE INVENTION

The invention offers a very advantageous solution to these problems.

The proposed pumping apparatus is of the type comprising an inlet duct, an outlet duct, at least one pump body having a chamber which communicates through inlet and outlet valves with these two ducts, a piston movable in a fluid-tight manner in this chamber, as well as a cyclic actuator of the rotary cam type co-operating with this piston to caust it to slide, and a motor driving the cam.

According to the invention, the motor is a finestep stepping drive unit, and associated therewith are control means suitable for regulating the movement of the stepping motor as a function of a required delivery and of a required return speed of the piston, and preferably as a function of a required angular path of travel of the cam during this return movement.

In a first embodiment, the required values for delivery, angular path of travel of the cam during the return travel, and speed of return are displayed with the aid of a device such as a set of coding wheels.

In another embodiment, a pressure pick-up is mounted on the outlet duct. The required values for delivery, return speed and a maximum outlet pressure are then displayed with the aid of a device such as a set of coding wheels, and the control means regulate the movement of the stepping motor so as additionally to maintain the outlet pressure approximately at the maximum displayed value. In a variant, it is also possible to record a minimum pressure, the falling short of which causes definitive stoppage of the pump.

Very advantageously, the pump body is interchangeable.

In accordance with a further feature of the invention, a position-detecting device co-operates with the cam to determine the end of the delivery stroke, this position detector being connected to control means.

In a preferred embodiment, the fine-step stepping drive unit comprises a stepping motor as such, associated with a pilot circuit, and the latter reacts to control signals by selectively passing, into the windings of the stepping motor, a current determined in accordance with a reference value which is in turn scaled in accordance with the control signals, so that the number of steps of the motor can be multiplied. Advantageously, the pilot circuit is capable of applying, to the individual windings of the stepping motor, a voltage which is periodically cut off, has a predetermined repetition rate and has a shape or form factor determined by comparison of the current passing through each winding with the reference value. Said circuit normally comprises a timer defining said predetermined rate of repetition. This arrangement constitutes an application of the teaching of U.S. patent application Ser. No. 089,191 filed Oct. 29, 1979 now U.S. Pat. No. 4,293,807 (corresponding to French patent application No. 78 31 023, filed Nov. 2, 1978).

In this application, the control means comprise a device adapted to count the required number of steps of the stepping motor, and thus to recognize its angular position, as well as a permanent memory means capable of associating, with each count, firstly, first digital signals the number of which is equal to that of the motor windings, and secondly, second digital signals, and the pilot circuit comprises switch means, arranged in series with each individual winding of the stepping motor and controlled by the respective one of the first digital signals, and at least one digital balancing network, controlled by the second digital signals, this network determining the scaling or gradation of the current in the individual windings.

In practice, each winding-switch assembly is arranged in series with a resistor, the voltage across which represents the current passing through the winding. The pilot or supply circuit comprises a comparator receiving, on the one hand, the voltage across this resistor and, on the other hand, the winding current scaled to the required value, and a feed means connected to the output of the comparator to supply the winding concerned so as to keep the actual winding current substantially at the required value.

If the windings of the stepping motor are grouped in pairs, and two windings of one pair cannot receive current at the same time, the resistor in series with the winding-switch assembly and the feed circuit are common to two windings of a same pair.

In accordance with a further feature of the invention, the control means comprise a general timer or clock, a micro-processor associated with fixed memories (ROMs) and direct-access memories (RAMs) as well as with an input/output interface forming a memory lock, connected to the pilot circuit of the stepping motor, the micro-processor generally reacting to the high timer frequency by defining the desired function of the stepping motor, whereas it reacts to interruptions of submultiple cadence in the timer frequency so as to effectively control the stepping motor.

Advantageously, the micro-processor controls the delivery stroke at the rate of at most one step per interruption, whereas it controls the entire return stroke during a same interruption during which the interruption signals are inhibited.

BRIEF DESCRIPTION OF THE DRAWINGS

Other features and advantages of the invention will be seen from perusal of the following detailed description referring to the drawings provided by way of a non-limiting example for the purpose of illustrating the presently preferred embodiment of the present invention. In the drawings.

DETAILED DESCRIPTION OF THE PREFERRED EMBODIMENTS

Figure 1:
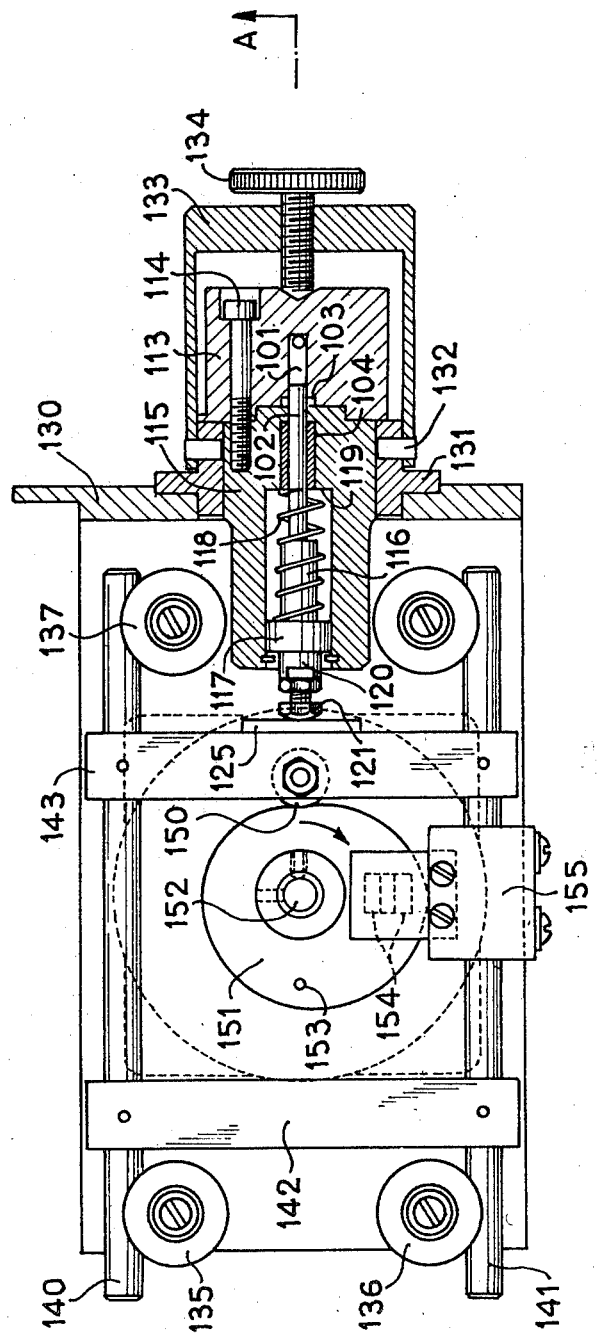
FIG. 1 is a horizontal section through the pumping apparatus of the present invention.
Figure 2:
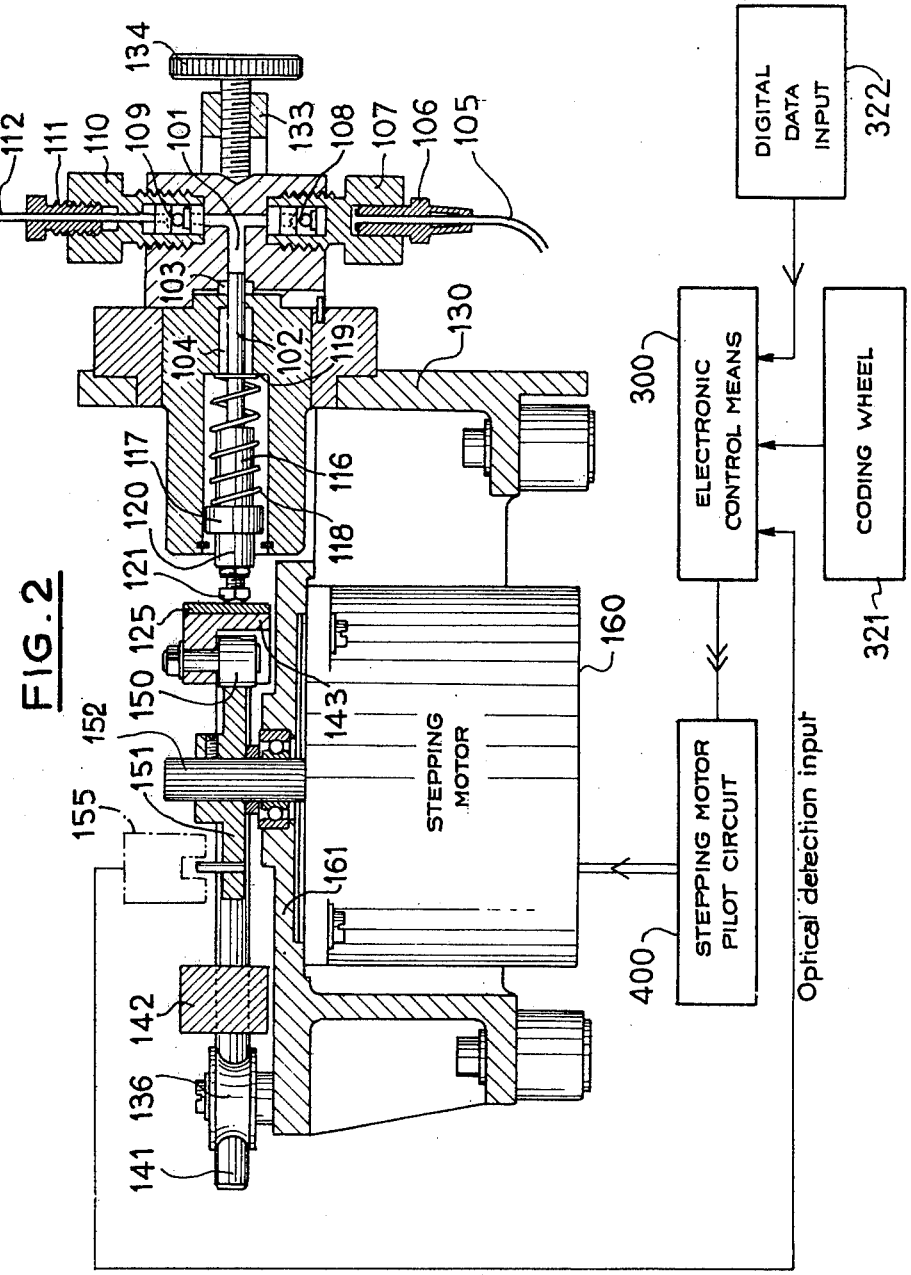
FIG. 2 is a vertical section through the same apparatus also comprising elements for driving the pump, namely the stepping motor, its pilot circuit and the electronic equipment controlling it.

The pumping apparatus illustrated in FIGS. 1 and 2 comprises a removable body consisting of the members 101 to 121.

The frame 130 of the apparatus comprises a flanged ring 131, provided with pivots 132 which carry a stirrup-shaped support 133 equipped with a knurled wheel 134. The pump-body assembly is fitted in the flanged ring 131, after which it is immobilized by lifting the stirrup-shaped member 133 and by actuating the knurled ring 134 which bears against the portion 113 of the pump body.

The pump body itself is made up of two portions 113 and 115 attached to each other by, for example, bolts such as that shown at 114. Formed between these two portions is a fluid-tight joint 103. Formed in the portion 113 is a cylinder 101 in which slides the piston 102 which is associated with the member 115, in which it slides in a cylindrical bearing 104.

In FIG. 2, the reference numeral 105 designates an inlet duct which is secured by means of a hermetic joint 106 to an inlet connection 107 equipped with a valve 108, the outlet of which communicates with the pumping cavity 101. On the outlet side, the pumping cavity 101 communicates, by way of a valve 109 forming part of the connexion 110, with an outlet duct 112 secured to this connexion 110 by means of a high-pressure joint 111.

It is important in the operation of the apparatus that the joint 103 as well as the valves 108 and 109 should be very fluid-tight. Advantageously, the joint 103 is a circular joint, the cross-section of which is in the form of a letter U lying on its side, and the base of which bears against the radial portion of the member 113, this joint itself enclosing an annular spring. The valves 108 and 109 advantageously incorporate ruby balls on a sapphire seat.

At its other end, the piston 102 has a head 116, followed by a shoulder 117 and then a further portion 120 having a diameter slightly greater than that of the portion 116. A spring 118 is fitted between the shoulder 117 and the radially narrowed portion 119 formed in the member 115, said spring constantly urging the piston towards the left. The portion 120, which is provided with an adjustable stop 121 formed for example by a screw having a counter-thread, then bears against a plate 125 which forms part of a carriage which will now be described.

The frame 130 of the apparatus carries two pairs of rollers 135 and 137, and 136 and 138. The two pairs of rollers are so arranged as to provide interior guide means for two parallel cylindrical rods 140 and 141 which form part of the above-mentioned carriage. Secured transversely on these rods are two bars 142 and 143 which complete the carriage. The bar 143 carries the above-mentioned plate 125 which urges the piston to the right against the bias of the spring 118. This bar 143 also carries a roller 150 which co-operates with a cam 151 mounted on a shaft 152.

The cam 151 carries a pin 153 adapted to pass between the two prongs of a fork 154. An infra-red beam passes continuously between the two prongs of this fork. The pin 153 interrupts the infra-red beam when it passes therethrough, and this is detected by an assembly 155 which, in response to such interruption, provides a logic signal called an "optical detection" signal which is passed to the electronic control means 300 (FIG. 2). It will be seen that when the pin 153 is detected by the means 154, 155, the top dead-centre of the cam co-operating with the roller 150, is reached, and the piston 103 is in its extreme right-hand position, which marks the end of the delivery stroke and the commencement of the return stroke of this piston.

As shown in FIG. 2, the cam-shaft 152 is actuated by the stepping motor 160, with which is associated a pilot circuit 400.

For performing the invention, it is very important that use is made of a stepping motor having fine steps. Very advantageously, such motor is provided by the arrangements described in the above-mentioned patent application. With these arrangements and on the basis of a stepping motor capable of executing 400 steps per revolution, it is possible for this number of steps to be multiplied. The above-mentioned patent application describes a stepping motor capable of 1200 steps per revolution, which is very suitable for performing the present invention without however excluding either slightly lower values or slightly greater ones.

Figure 4:
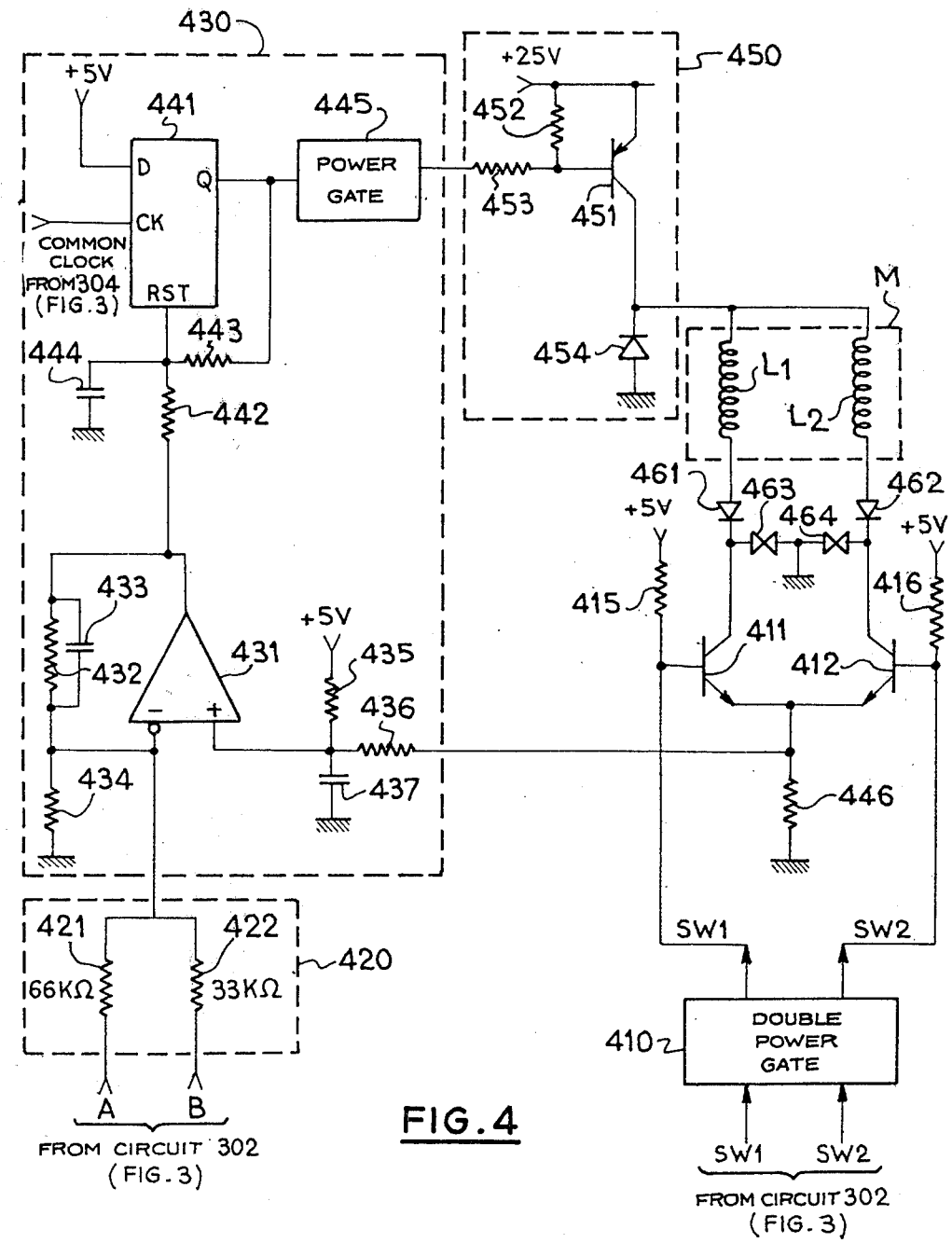
FIG. 4 is a detailed electrical diagram illustrating part of the pilot circuit of the stepping motor 400 of FIGS. 2 and 3.

In a particularly preferred embodiment, the stepping motor 160 is therefore one capable of 400 steps, such as the SLO-SYN (Registered Trade Mark) MO91-FDO6 motor, produced by the American Company, Superior Electric. This motor comprises four windings which may be designated L1 to L4. The pilot circuit 400 of this motor comprises, in duplicate, the structure illustrated in FIG. 4 of the present patent application, which corresponds to FIG. 4 of the above-mentioned earlier patent application. The arrangement illustrated in this FIG. 4 is suitable for two windings, and it is therefore used in duplicate to meet the requirements of four windings of the stepping motor. The contents of the above-mentioned earlier patent application are hereby incorporated in the present description to enable the apparatus illustrated in FIG. 4 to be understood and described. It will be noted that the numerical references of the present FIG. 4 and the FIG. 4 of the earlier patent application are identical with the exception of the hundreds, which have been altered to correspond to the figures used herein.

Instead of being directly controlled by a permanent memory as is the case in the earlier patent application, the pilot circuit 400 is here controlled by an electronic control means comprising a micro-processor 300. As will be seen later, this means 300 also comprises a permanent memory capable of accommodating the matching table shown in the aforementioned patent application.

For the purpose of applying it to the pump of the present invention, the electronic control means 300 comprises various inputs, one of which is a display input 321, using, for example, coding wheels, a second input 322 being for digital data which may derive from a digital monitoring assembly or from any other source of digital information, and finally a third optical detection input which is provided by the circuit 155 which detects the end of the delivery stroke and the commencement of the return stroke of the piston.

Figure 3:
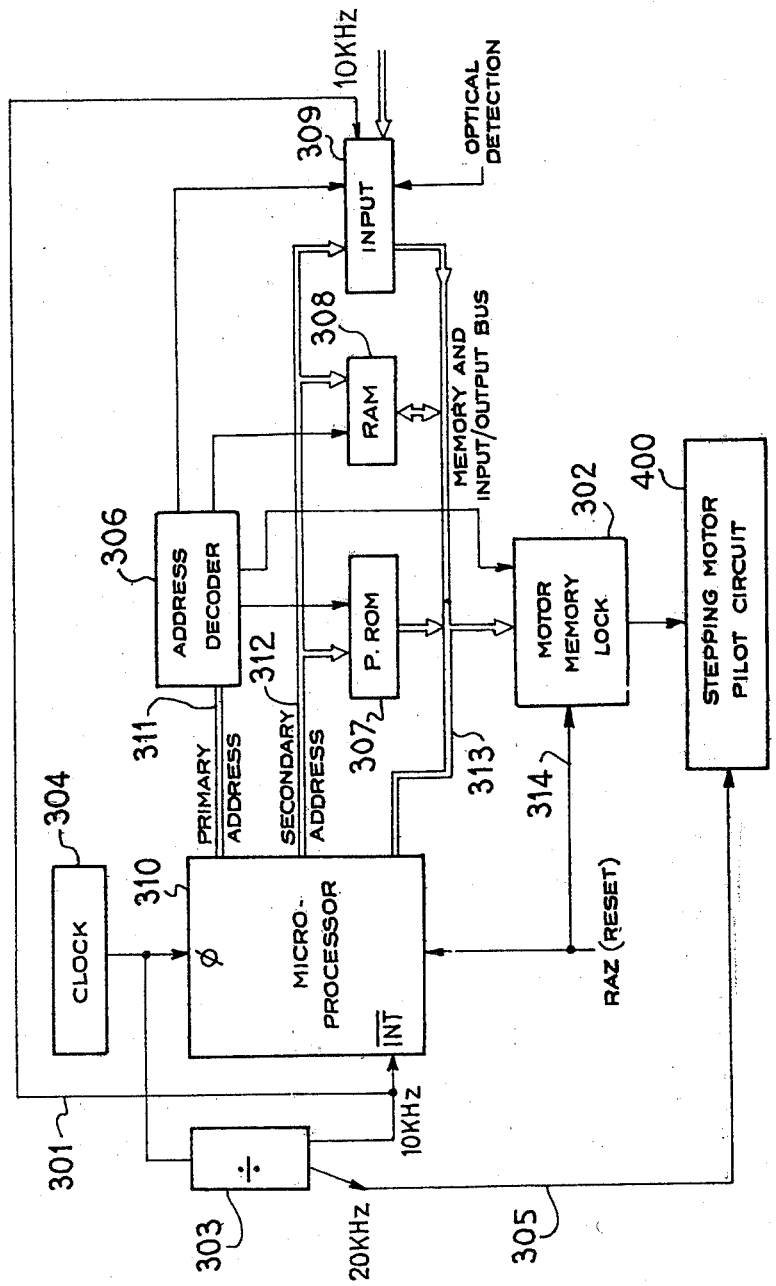
FIG. 3 is a schematic electrical diagram showing the electronic control means 300, this Figure also including the pilot circuit 400 of the stepping motor, but not in detail.

FIG. 3 illustrates the architecture of the electronic control means 300, as well as its connexions with the pilot circuit of the stepping motor 400.

A timer or clock 304 feeds a micro-processor 310 as well as a dividing circuit 303 which provides, at a first output pulses at 10 KHz. These are applied, on the one hand, directly to the interruption input INT of the micro-processor 310, and on the other hand, to an input interface 309 by way of a line 301. A second output 305 of the divider 303 provides 20 KHz pulses which are applied to the pilot circuit of the stepping motor 400, and are utilized in the manner described in the above-mentioned earlier patent application.

The micro-processor is able to deliver address signals along the lines 311 and 312. The line 311 carries the primary address which is applied to an address decoder 306, which consequently chooses to energize the programmable permanent memories 307, or the random access memories 308, or the input interface 309. These same circuits receive detail or secondary address signals determined by the line 312 which is connected to each of them.

The signals between the circuits 307, 308 and 309 are communicated by way of an input/output and memory busbar 313 connected to each of these circuits as well as to the micro-processor. The address decoder 306 is also capable of addressing the memory-lock circuit 302 of the motor, which is also connected to the input/output busbar 313. This memory circuit 302 will receive digital signals provided by the micro-processor for controlling the pilot circuit of the stepping motor. These digital output signals are provided in accordance with the teachings of the above-mentioned patent application. Finally, a line 314 enables the micro-processor 310 and the memory-lock circuits 302 to be jointly reset.

Without entering into details, at least one portion of the programmable permanent memories 307 comprises a table for controlling the stepping motor, this table resembling that described in the above-mentioned patent application. As will be seen below, the microprocessor makes decisions regarding the forward movement of the stepping motor, and once this decision is made, it actuates the memory-lock 302 in a manner corresponding to the contents of the table of the memory 307 concerned. It is thus seen how the microprocessor 310 is able to control the stepping motor in the manner described in the earlier patent application. There remain to be seen the systems whereby the micro-processor 310 arrives at decisions regarding the advance of the stepping motor and therefore of the pump, which systems are specific to the present invention which uses the other elements described above.

For this purpose, the memories 307 comprise a series of steps determining a main programme illustrated in FIG. 5, and a series for this programme illustrated in FIGS. 6, 7, 8 and 9.

The memory needs of these various methods are met with the aid of the random-access memory 308, and these methods call on the input signals available at the interface 309.

Referring to FIG. 5, the principal programme simply consists of a loop which calls in different sub-programmes in sequence. The steps 501 consists in calls in a sub-programe of external data determined by the circuit 322 of FIG. 2. The step 502 consists in calling in the reading of the interruptors or coding wheels forming the display circuit 321 of FIG. 2. The step 503 consists in calling in a conventional programme for converting signals in a binary decimal code into pure binary signals. The steps 504 consists in calling in a speed-limit programme which will be described by reference to FIG. 6. The step 505 consists in calling in an acceleration-limit programme which will be described by reference to FIG. 7, and the step 506 consists in a call-in programme for fixing speed which will be described by reference to FIG. 9.

The sub-programme called in by the steps 501 and 502 consists in a simple treatment of data which are either of external origin or are determined by the coding wheels. The programme concerned is one of sequential treatment which may be carried out in the conventional manner known to the expert in the field.

It will simply be noted that in a first embodiment of the invention, use is mainly made of data displayed by means of an interruptor, and optionally external data. In such a case, the coding wheels display the required value for delivery in the form of a hundreds figure, a tens figure and a units figure, and the required value for the return stroke, in the form of one or more decimal figures, to which can be caused to correspond a memorized plurality of predetermined values for the return stroke, and in the same way, the value for the return speed which may be coded with the aid of one or more figures, to which can be caused to correspond one or more memorized values of the return speed.

After the external data have been collected at the step 501, and the display decimal data at the step 502, and the latter have been converted into binary form at the step 503, the principal programme then calls in the step 504, for speed limit, illustrated in FIG. 6.

At the step 601, first is calculated a value Tcc, which determines the time for the complete cycle of the pump. This calculation is carried out by using, on the one hand, the delivery display on the coding wheels, and, on the other hand, the number of programmed interruptions which corresponds to the unit of delivery. It will be seen later that the interruptions are directly related to the delivery of the pump.

The step 602 in turn calculates the delivery time $T_{RF}$, obtained from the difference between the time for the complete cycle Tcc and the return time $T_{RTR}$. It will be seen later that the return time is determined by the speed-determining step 506.

The delivery time $T_{RF}$, calculated at the step 602, is then compared, at the step 603, with a minimum value, programmed as defining the minimal possible delivery time. If the value calculated is less than the minimal time, the step 605 authoritatively fixes the delivery time at the minimum value. If it is higher, one passes directly to the step 606, which deduces from the delivery time the delivery speed $V_{RF}$. Here again, this brings in the value for the delivery stroke which will be determined in the steps of FIG. 9.

Figure 7:
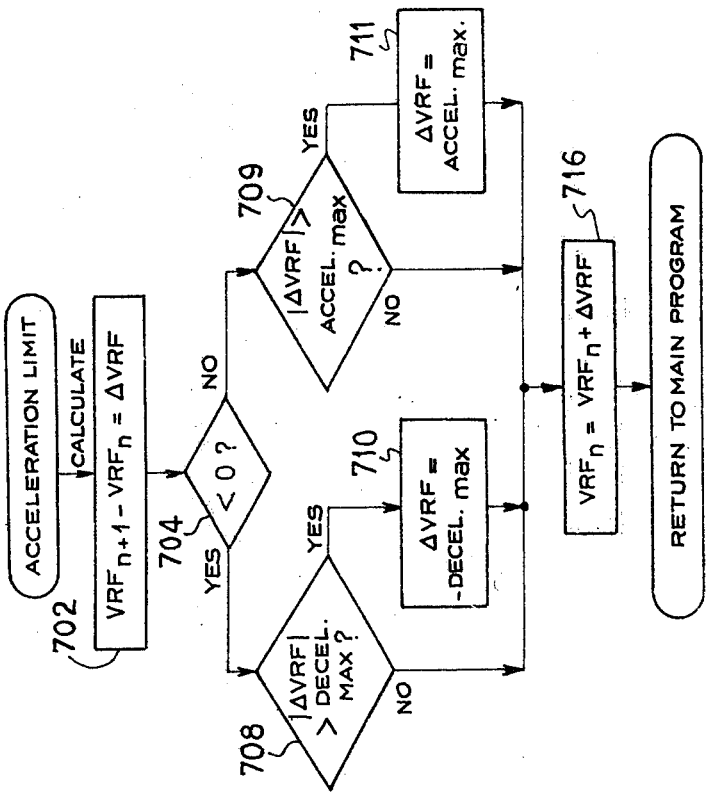

In turn, the delivery speed $V_{RF}$ is compared, at the set 608, with a maximum acceptable value. If it is greater, the step 609 authoritatively fixes the delivery speed at this maximum value. If it is lower, it passes directly to the step 610 which consists in transferring to the memory the result $V_{RF}$ obtained. One then returns to the main programme which then calls in the sub-programme for the acceleration limits, at step 505. This is illustrated in FIG. 7.

At the step 702, there is first calculated the difference between the new delivery speed values and the earlier values, which difference is designated $\Delta V_{RF}$. The step 704 determines whether this speed difference is positive or negative, that is to say whether an acceleration or a deceleration is involved.

In the case of a deceleration, the step 708 compares the speed increment with a maximum value which corresponds to a maximum deceleration. If the speed increment, in absolute value, is found to be less than the maximum deceleration, one passes directly to the step 716. Otherwise, the step 710 fixes the speed increment at a negative value equal to that corresponding to the maximum deceleration.

In the event of acceleration, the step 709 compares the speed increment with a value defining the maximum acceleration. As previously, if the acceleration is permissible, one passes directly to the step 716; otherwise the step 711 fixes the speed increment at the positive value corresponding to the maximum acceleration.

Thereafter, the step 716 takes, as the new delivery speed value, the preceding value increased by the speed increment selected, and one returns to the principal programme.

Figure 8:
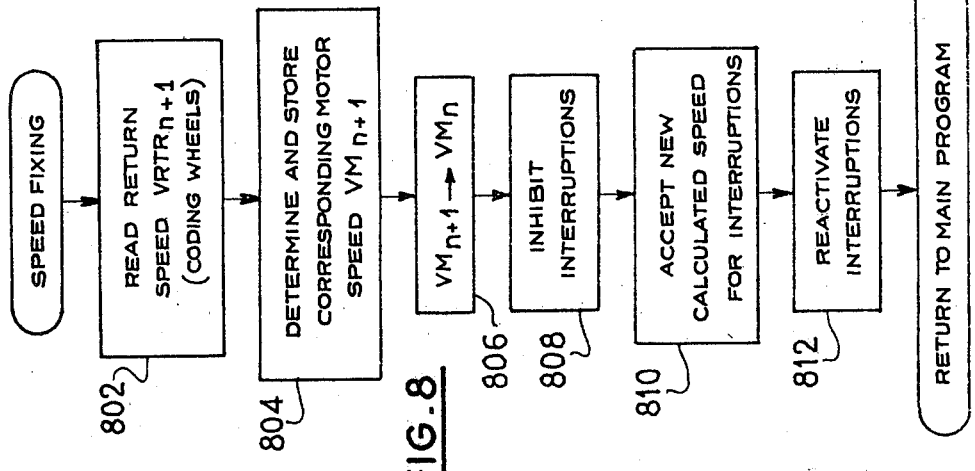

The principal programme then calls in, at its last step 606, the speed-fixing sub-programme, which is shown in FIG. 8.

Its first stage 802, which is isolated, consists in reading the return speed which corresponds to the value displayed on the coding wheels. It will be recalled that the coding wheels display only an indication of return speeds that is translated into speed with the aid of a matching table which can be recorded in one of the permanent memories 307 (FIG. 3).

The following step 804, independent of the previous one, uses the new delivery speed value so as to determine and store a corresponding motor speed designated $VM_{n+1}$. The following step 806 transfers this value $VM_{n+1}$ as the current value of the motor speed, designated $VM_n$.

The following step 808 inhibits the interruption process. The next step 810 causes the new value, calculated as the motor speed $VM_n$, to participate in the interruption process so that it can be used to determine the advance of the motor as will be seen below by reference to FIG. 9. Then, the step 812 reactivates the interruption process. It will be seen in effect that it is desirable to break off the interruption process when its main parameter is modified, namely the speed of the motor. After the step 812, one returns to the principal programme.

The micro-processor normally carries out the principal programme illustrated in FIG. 5, with its differences from the programmes, and in particular those described by reference to FIGS. 6 to 8. At its input $\overline{INT}$ (FIG. 3), it periodically receives 10 KHz pulses which cause interruptions.

These interruptions correspond to the delivery stroke of the motor, one step of which can be controlled at each interruption. On the other hand, at the time of the return stroke, the interruptions are inhibited as will be seen hereinafter.

Figure 9:
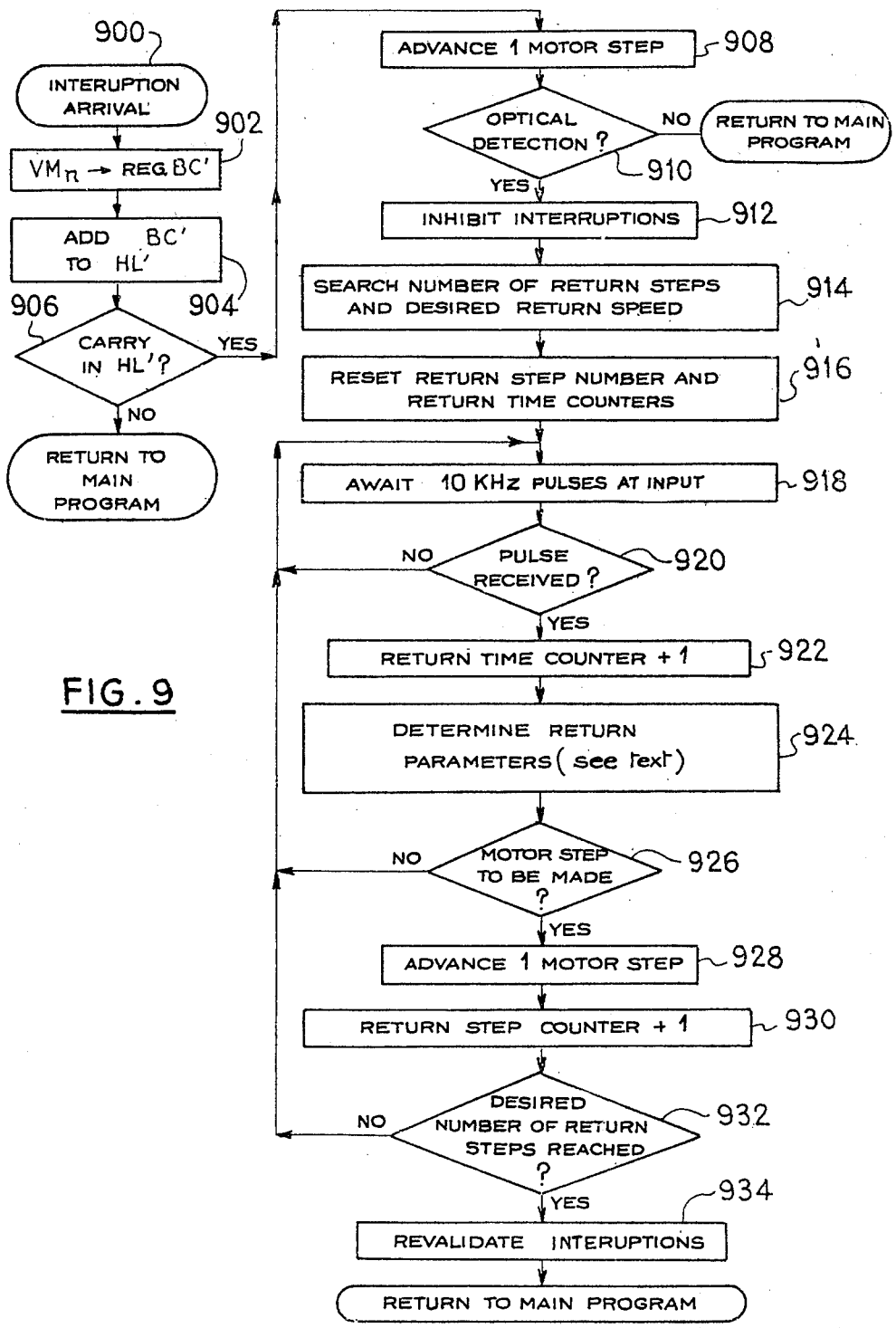

The control of the stepping motor with the aid of the interruption process is illustrated by FIG. 9. Its first step 900 defines the arrival of an interruption. The step 902 causes the value, determined for the speed $VM_n$ of the motor, to be entered in a register BC'. Then, at the next step 904, the microprocessor adds the value contained in the register BC' to a register HL'. Each time that the capacities of this register HL' are recorded as having been exceeded, that is to say at each carry-over, the step 906 decides to advance the motor by one step. Otherwise, one returns to the principal programme.

The register 904 constitutes a digital store for the requiring values for the motor speed, performing the function of a digital time constant. In view of the fact that the interruptions occur at a regular rate during the delivery operation, it will be immediately seen that the advance of the motor will be proportionate to the contents of the register BC'.

While the motor is executing its delivery stroke, one returns to the principal programme after the motor has possibly advanced one step. This condition causes intervention of the optical detection means 155 (FIGS. 1 and 2), the output of which is applied to the input members 309 (FIG. 3). In the absence of optical detection, the pump moves to the delivery position, and the test by the step 910 then causes this return to the principal programme. On the other hand, following the completion of the delivery stroke, an optical detection is recorded and at the last motor step in the delivery stroke, the process of FIG. 9 passes to the step 912 instead of returning to the principal programme. It is of course necessary that the useful detection time of the device 155 should be greater than one step of the motor.

At the beginning of the return stroke, the step 912 commences by immediately inhibiting the interruption process, so blocking the operation of the microprocessor so that it carries out only the following steps without now taking into account the interruptions.

The following the step 914 seeks out the number of return steps and the desired return speed that have been read on the coding wheels. Step 916 resets a counter of the number of return steps, as well as a counter of the return time.

Then at the step 918, the micro-processor is made ready for receiving 10 KHz pulses which are similar to the interruption impulses, but which arrive at the input circuit 309 of FIG. 3, by way of the line 301. As the step 920 indicates, as long as no pulse is received, the microprocessor remains at the ready. On the other hand, as soon as it receives a 10 KHz pulse, it begins, at the step 922, by advancing, by one unit, the return-time counter.

Then at the step 924, the micro-processor determines the return parameters, taking into account the preceeding speed of the stepping motor and the required return speed. Very advantageously, the return stroke comprises an acceleration phase and a deceleration phase for reaching the threshold constituted by the required return speed, this threshold in turn being followed by a deceleration and braking phase which returns to the normal required motor speed during the delivery stroke, which speed has of course been fed into a memory. These acceleration and deceleration phases of a stepping motor are regarded as being known to the expert in the field and will not be described in detail, although they comprise a quite large number of operations. Different variations can be used in this connexion without departing from the framework of the invention.

The parameters of the return movement of the motor and the pump having thus been determined at the step 924, the step 926 determines whether the motor should make a step. If it should, the step 928 advances the motor by one step. Otherwise, one returns directly to the waiting condition determined by the step 918. After the motor has possibly advanced by one step at the stage 928, the stage 930 causes an increase, by one unit, in the return-step counter. This stage is followed, at 932, by a comparison of the contents of this counter with the required number of return steps as has been read off at the step 914 and displayed by the coding wheels. If the required number of return steps has not been reached, one returns to stage 918. If, on the contrary, the required number of return steps has been reached, the return stroke is then terminated, and one returns to the principal programme after having re-established the interruption process at the step 934.

The above-mentioned flow charts or ordinograms are simplified in certain respects, particularly as regards the establishment of the initial conditions that is regarded as being within the capabilities of the person skilled in the art, once the essential make-up of the process has been provided The pumping apparatus that has been described offers important advantages.

It is known that liquid-phase chromatography can cause the intervention of stationary phases, the pressuredrop of which varies over a wide range, as well as of solvents having very different physical properties. If the function of defining the delivery stroke is left to the single cam, the delivery pressure will depart from the corresponding value at the maximum return point of the piston and will increase until the maximum advance point of the piston is reached. In the general case, the initial delivery pressure is low in relation to the pressure to which the chromatography installation is brought at the time of the preceding stroke, and very considerable fluctuations in pressure result.

With the aid of a manual display in this first embodiment, or with the aid of a downstream pressure pick-up in a second embodiment, the invention first makes it possible to adjust the angular stroke of the cam on return, so as to minimize the fluctuations in pressure.

Furthermore, the invention permits an extremely precise regulation of the delivery of the pump, whatever its operating conditions as regards pressure, this also being fundamental.

In a second embodiment of the invention, which makes use of a downstream pressure pick-up, regulation of pressure is still more precise, and is automatic.

The pressure pick-up (not illustrated) is an analogue pick-up associated with an analogue-to-digital converter, the outputs of which are connected to the input circuit 322 for external digital data (FIG. 2).

On the other hand, the coding wheels display the delivery and the return speed, as before, but not the angular stroke of the cam on return. Furthermore, a maximum output pressure is displayed and, advantageously, a minimum output pressure.

The remaining differences between the second and first embodiments are mainly concerned with the control means, and will be described hereinafter by reference to FIGS. 5A and 6A which show variants of the arrangements shown in FIGS. 5 and 6.

Figure 5A:
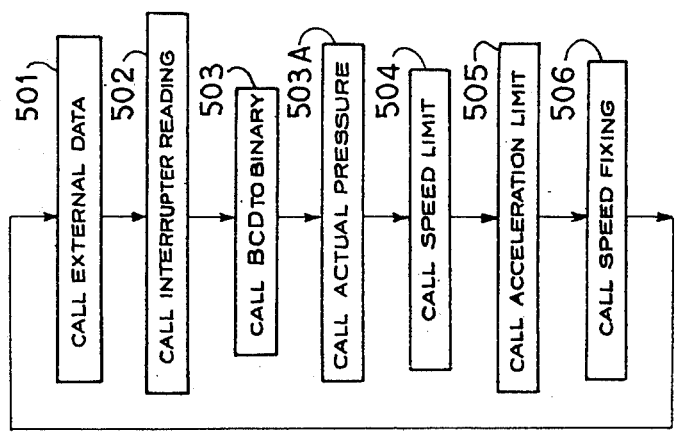

Between the steps 503 and 504, FIG. 5A has a step 503A "call actual pressure", which comprises the following operations:

Reading of the actual downstream pressure as given at the output of the analogue-to-digital converter associated with the pressure pick-up;

Comparison of the new value for actual pressure with the preceding value;

If it is lower, the addition of a predetermined number of steps to the return stroke;

If it is higher, the deduction of a predetermined number of steps from the return stroke;

Determination of a corrected delivery speed $V_{RFPR}$, taking into account the actual pressure and the maximum displayed pressure (by applying a predetermined amplification to the difference between the two pressures).

Figure 6A:
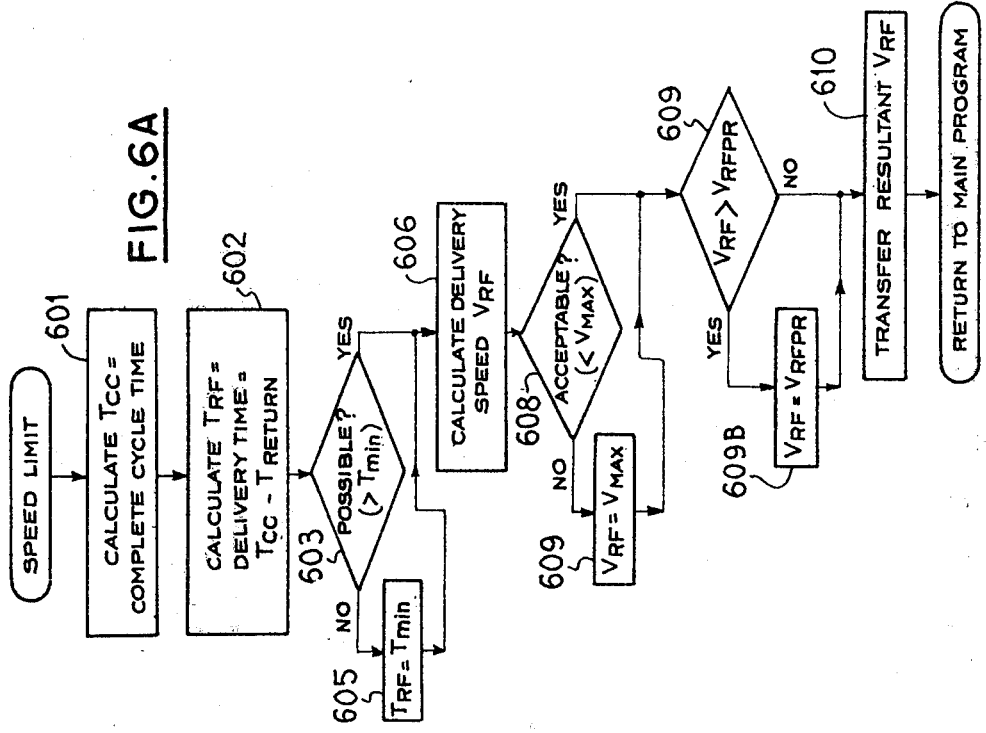
FIGS. 5 to 9 are flow charts illustrating various sequences of operations carried out by the electronic control means 300 of FIGS. 2 and 3.

At the next step 504 of the principal programme, and as shown in FIG. 6A, there will be a supplementary stage 609A for comparing the envisaged delivery speed $V_{RF}$ with the above-mentioned value $V_{RFPR}$. If the first is higher than the second, the additional stage 609B makes $V_{RF} = V_{RFPR}$.

Whereas the first embodiment comprises only controlling the delivery and a manual adjustment of the pressure fluctuations (by way of the angular return stroke of the cam), the second embodiment effects control of, first, delivery and then, pressure, when the maximum displayed pressure is reached. Furthermore, it also adjusts the number of steps in the angular return stroke of the cam, as previously indicated.

Finally, there is also provision (at step 503A for example) for a comparison of the actual downstream pressure with the minimum displayed pressure; if the first is lower than the second (occurring for example if there is a downstream break in the line), the pump is definitely stopped for safety's sake.

These advantages result in the pumping apparatus in accordance with the present invention being able to supply chromatography installations under conditions in which delivery and pressure are very well defined and practically free from fluctuations.

It will also be known that hitherto the jerky movement of stepping motors has been considered highly undesirable in applications such as chromatography. The use of a fine-step stepping motor, as in the present invention, overcomes this prejudice, while greatly increasing the possible uses of chromatography.

The invention has a further interesting feature. It has been noted in connexion with FIGS. 1 and 2 that the pump body is readily removable with the aid of the stirrup-shaped member 133 and the knurled wheel 134. Thus, various pump bodies having variable sections and capacities can be used. This further increases the possible uses of the pumping apparatus in chromatography.

It is then necessary to record, in the memory, the characteristics of the various pump bodies that may be used. The selection, by the micro-processor, of the characteristics of the pump body fitted may be carried out either with the aid of a new display coding wheel, or with the aid of a marking made on the pump body itself and automatically transcodable in digital form so that it can be directly used by the micro-processor.

The present invention is not of course limited to the arrangements described, and it covers all variants falling within the spirit of the invention.

In particular, it is not limited by the particular form of the steps illustrated in FIGS. 5 to 9, which the expert will be able to amend while preserving the essential characteristics. It is also possible, for very simplified uses, to replace the memorized system by a cabled logic system.

Also, the invention has been described by reference to a single-piston pump wherein the fluctuations in pressure and delivery can be considerably reduced. The same advantages can of course be obtained with a mulitiple-piston pump, which also then provides better performance.

What is claimed is:

1. In pumping apparatus of the type comprising an inlet duct, an outlet duct, at least one pump body having a chamber which communicates through inlet and outlet valves with these two ducts, a piston movable in a fluid-tight manner in this chamber, as well as a cyclic actuator of the rotary cam type co-operating with this piston to cause it to slide, and a motor driving the cam, the improvement in which the motor is a fine-step stepping drive unit, and associated therewith are control means suitable for regulating the movement of the stepping motor as a function of a required delivery flow rate and as a function of a required stroke and return speed of the piston, said fine-step stepping drive unit comprises a stepping motor as such, associated with a pilot circuit, and the latter reacts to control signals by selectively passing into the windings of the stepping motor a current determined in accordance with a reference value which is in turn scaled in accordance with the control signals, this enabling the number of motor steps to be multiplied, said pilot circuit is adapted to apply to the individual windings of the stepping motor a periodically cut-off voltage of predetermined repetition rate and having a form factor defined by comparison of the current passing through each winding with the reference value.

2. Pumping apparatus according to claim 1, in which the required values for delivery and for the return stroke and return speed are displayed with the aid of apparatus such as coding wheels.

3. Pumping apparatus according to claim 1, in which a pressure pick-up is mounted on the outlet duct, and the required values for delivery, return speed and a maximum outlet pressure are displayed with the aid of equipment such as coding wheels, the control means regulating the movement of the stepping drive unit so as also to keep the outlet pressure close to the displayed maximum value.

4. Pumping apparatus according to claim 1, in which the pump body is interchangeable.

5. Pumping apparatus according to claim 1, including a position-detecting device co-operating with the cam so as to determine the end of the delivery stroke, this position-detector being connected to control means.

6. Pumping apparatus according to claim 1, in which the pilot circuit comprises a timer defining said predetermined repetition rate.

7. Pumping apparatus according to claim 1, in which each winding-switch assembly is arranged in series with a resistor, the voltage across which represents the current passing through the winding.

8. Pumping apparatus according to claim 7, in which the pilot circuit comprises a comparator to which is applied, on the one hand, the voltage across this resistor and, on the other hand, the winding current scaled to the required value, and a feed means connected to the output of the comparator to supply the winding concerned so as to keep the actual winding current substantially at the required value.

9. Pumping apparatus according to claim 7, wherein the windings of the stepping motor are grouped in pairs, and two windings of a same pair cannot be brought into the circuit at the same time, the resistor in series with the winding-switch assembly and the feed circuit being common to two windings of a same pair.

10. Pumping apparatus according to claim 1, in which the control means comprise a timer, a micro-processor associated with fixed memories and random-access memories, as well as with an inlet/outlet interface and an interface forming a memory lock connected to the pilot circuit of the stepping motor, and the micro-processor generally reacts to a high timer frequency by defining the desired function of the stepping motor, whereas it reacts to interruptions of sub-multiple cadence in the timer frequency by deffectively controlling the stepping motor.

11. Pumping apparatus according to claim 10, in which the micro-processor controls the delivery stroke at a rate of at most one step per interruption, whereas it controls the entire return stroke during a same interruption during which the interruption signals are inhibited.

12. In pumping apparatus of the type comprising an inlet duct, an outlet duct, at least one pump body having a chamber which communicates through inlet and outlet valves with these two ducts, a piston movable in a fluid-tight manner in this chamber, as well as a cyclic actuator of the rotary cam type co-operating with this piston to cause it to slide, and a motor driving the cam, the improvement in which the motor is a fine-step stepping drive unit, and associated therewith are control means suitable for regulating the movement of the stepping motor as a function of a required delivery flow rate and as a function of a required stroke and return speed of the piston, said fine-step stepping drive unit comprises a stepping motor as such, associated with a pilot circuit, and the latter reacts to control signals by selectively passing into the windings of the stepping motor a current determined in accordance with a reference value which is in turn scaled in accordance with the control signals, this enabling the number of motor steps to be multiplied, said control means comprise a device adapted to count the number of required steps of the stepping motor and thus to recognise its angular position, as well as permanent memory means capable of associating, with each count, firstly, first digital signals of a number equal to that of the motor windings, and secondly, second digital signals, and the pilot circuit comprises switch means, arranged in series with each individual winding of the stepping motor and controlled by the respective one of the first digital signals, and at least one digital balancing network, controlled by the second digital signals, this network determining the scaling of the current in the individual windings.

* * * * *

UNITED STATES PATENT OFFICE
CERTIFICATE OF CORRECTION

Patent No. 4,326,837   Dated April 27, 1982

Inventor(s) Robert E. Gilson; George W. Foster; Alain M. Bonneyrat

It is certified that error appears in the above-identified patent and that said Letters Patent are hereby corrected as shown below:

Column 12, line 26, delete "deffectively" and insert --effectively--.

Signed and Sealed this

Seventh Day of September 1982

[SEAL]

Attest:

GERALD J. MOSSINGHOFF

Attesting Officer   Commissioner of Patents and Trademarks